United States Patent
Wake

(10) Patent No.: US 9,078,434 B2
(45) Date of Patent: Jul. 14, 2015

(54) ANTIMICROBIAL POUCH

(76) Inventor: Kiyohiro Wake, Hiratsuka (JP)

( * ) Notice: Subject to any disclaimer, the term of this patent is extended or adjusted under 35 U.S.C. 154(b) by 0 days.

(21) Appl. No.: 13/479,956

(22) Filed: May 24, 2012

(65) Prior Publication Data

US 2013/0066294 A1    Mar. 14, 2013

(30) Foreign Application Priority Data

Sep. 8, 2011   (JP) ................. 2011-195716

(51) Int. Cl.
*A61J 1/05*     (2006.01)
*A01N 25/34*    (2006.01)
*A61J 1/00*     (2006.01)
*A01N 25/08*    (2006.01)

(52) U.S. Cl.
CPC ............... *A01N 25/34* (2013.01); *A01N 25/08* (2013.01); *A61J 1/00* (2013.01)

(58) Field of Classification Search
CPC ........... A61J 1/00; A61K 8/02; A61K 8/0204; A61K 8/0225; A61L 2/00; A61L 2/23; A61L 9/00; A61L 9/01; A61L 9/04; A61L 9/042; A61L 9/12; A61Q 15/00; A01N 25/08; A01N 25/34
USPC .......................................... 604/410, 359–360
See application file for complete search history.

(56) References Cited

U.S. PATENT DOCUMENTS

2010/0282263 A1   11/2010   Asada et al.

FOREIGN PATENT DOCUMENTS

| JP | 59-048402 | | 3/1984 | | |
|----|-----------|---|--------|---|---|
| JP | 60-161307 | | 8/1985 | | |
| JP | 62-119938 | * | 7/1987 | ............... | A61L 9/12 |
| JP | 62-119938 U | * | 7/1987 | ............... | A61L 9/12 |
| JP | 63-022501 | | 1/1988 | | |
| JP | 63-130045 | | 8/1988 | | |
| JP | 03-050025 | | 5/1991 | | |
| JP | 03-126143 | | 12/1991 | | |
| JP | 04-016180 | | 3/1992 | | |
| JP | 06-233985 | | 8/1994 | | |
| JP | 6-233985 | | 8/1994 | | |
| JP | 06-233985 A | * | 8/1994 | ............... | C02F 1/50 |
| JP | 06-065402 | | 9/1994 | | |

(Continued)

OTHER PUBLICATIONS

English machine translation of JP 06-065402A. Retrieved from JPO on Jul. 9, 2013.*

(Continued)

Primary Examiner — Philip R Wiest
Assistant Examiner — Benjamin Klein
(74) Attorney, Agent, or Firm — Hamre, Schumann, Mueller & Larson, P.C.

(57) ABSTRACT

Provided is a solid antimicrobial agent suitable for portable use, which can continuously release a stable amount of chlorine dioxide even under vibration or shock. An antimicrobial pouch includes: an antimicrobial agent supporting an antimicrobial substance in a porous inorganic solid carrier; a first pouch body receiving the antimicrobial agent; and a second pouch body receiving the first pouch body, wherein the first pouch body includes fine holes on an entire surface, the fine holes having a diameter smaller than a particle size of the inorganic solid carrier, and the second pouch body includes release holes at an edge portion, the release holes through which the antimicrobial substance is released to atmosphere of the second pouch body.

15 Claims, 3 Drawing Sheets

(56) References Cited

FOREIGN PATENT DOCUMENTS

| | | | | |
|---|---|---|---|---|
| JP | 06-065402 A | * | 9/1994 | ............ A01N 25/18 |
| JP | 06-065402 U | * | 9/1994 | ............ A01N 25/18 |
| JP | 09-299462 | | 11/1997 | |
| JP | 10-167323 | | 6/1998 | |
| JP | 10-278970 | | 10/1998 | |
| JP | 2003-055120 | | 2/2003 | |
| JP | 2003-148861 | | 5/2003 | |
| JP | 2003-159317 | | 6/2003 | |
| JP | 3112293 | | 6/2005 | |
| JP | 2008-200208 | | 9/2008 | |
| JP | 2008200208 A | * | 9/2008 | ............ A61L 9/00 |
| JP | 3154094 | | 9/2009 | |
| WO | 2009/051018 | | 4/2009 | |

OTHER PUBLICATIONS

English machine translation of JP 06-233985A. Retrieved from JPO on Jul. 9, 2013.*

English Machine Translation of JP-2008-200208-A.*

English machine translation of JP 06-065402U. Retrieved from JPO Jul. 9, 2013.*

* cited by examiner

ANTIMICROBIAL POUCH

BACKGROUND OF THE INVENTION

1. Field of the Invention

The present invention relates to an antimicrobial pouch. More specifically, the present invention relates to an antimicrobial pouch in which an antimicrobial agent supporting an antimicrobial substance in a porous inorganic solid carrier is received in a pouch body.

2. Description of the Related Art

Recently, chlorine dioxide has received attention as a sterilizing antimicrobial agent replacing chlorine. In the past, as a method of generating chlorine dioxide, a mixing reaction of a sodium chlorite aqueous solution (stabilizing chlorine dioxide aqueous solution) and an acid (activating agent) was mainstream (See Japanese Patent Application Laid-Open (JP-A) No. 60-161307). However, such a method has not been easily used by a general user because a mixing is time-consuming and it is likely to cause a side reaction.

As a technology for solving such problems, a sterilizing antimicrobial agent produced by an adsorptive retention of chlorine dioxide gas in a porous inorganic carrier was developed (See JP-A No. 6-233985). JP-A No. 6-233985 discloses that the sterilizing antimicrobial agent is stored while being filled in a container, and chlorine dioxide is slowly dispersed in air through an opening portion by opening a top lid of the container.

On the other hand, the following is known as a case or pouch receiving a medical agent such as an antimicrobial substance or the like. For example, it is known a slow-release medical agent receiving body in which a slow-release medical agent is stored in a pouch made of a gas impermeable sheet, an opening is formed in the pouch, and a medical agent release film is formed in the opening (See JP-A No. 10-167323). Also, it is known that a deodorizer is encapsulated in a water-shedding non-woven fabric and is stored in a resin cassette installed in a refrigerator (See JP-A No. 2003-148861).

SUMMARY OF THE INVENTION

In the case in which the sterilizing antimicrobial agent disclosed in JP-A No. 6-233985 is applied to a product suitable for portable use, a stable continuous release of chlorine dioxide is required in terms of stability and persistence of effects, without leakage of a carrier supporting chlorine dioxide or generation of high-concentration chlorine dioxide at a time, even though strong vibration or shock is given to a product.

In other words, if the product based on the stationary use as described in JP-A No. 6-233985 is simply diverted for a portable use, the safety may not be sufficiently secured and the persistence of the effect is deficient.

Therefore, the invention is directed to provide a solid antimicrobial agent suitable for portable use, which is capable of continuously releasing a sustained amount of an antimicrobial substance such as chlorine dioxide even under vibration or shock.

To solve the above problems, an antimicrobial pouch includes: an antimicrobial agent supporting an antimicrobial substance in a porous inorganic solid carrier; a first pouch body receiving the antimicrobial agent; and a second pouch body receiving the first pouch body, in which the first pouch body includes fine holes on an entire surface, the fine holes having a diameter smaller than a particle size of the inorganic solid carrier, and the second pouch body includes a release hole through which the antimicrobial substance is released to atmosphere.

The antimicrobial agent constructed as above releases the antimicrobial substance between the first pouch body and the second pouch body through the fine hole of the first pouch body, and continuously releases an appropriate amount of the antimicrobial agent to atmosphere through the release hole of the second pouch body.

In an exemplary embodiment of the present invention, the second pouch body is provided with a hole used for suspending the second pouch body.

Accordingly, the antimicrobial pouch can be carried by wearing it around a neck, hanging it to a bag with a string or a strap through the hole in the antimicrobial pouch, or a clip-attached strap.

In an exemplary embodiment of the invention, the second pouch body includes a space in a region where the first pouch body contacts an inside of the second pouch body, and a space between the first pouch body and the second pouch body, and the release hole is provided in a region where the spaces of the second pouch body are formed.

In the second pouch body, the release hole is provided in the region where the space is formed between the first pouch body and the second pouch body. Therefore, the antimicrobial substance can be stably released using a flow of air introduced from the release hole.

The antimicrobial pouch constructed as above can retain the antimicrobial substance, which is released to the outside of the first pouch body, in the space between the first pouch body and the second pouch body, and can also release the antimicrobial substance to atmosphere from the release hole formed in the space. Therefore, even when strong vibration or shock is applied, it is possible to suppress the antimicrobial substance from being released to atmosphere at a time.

On the other hand, the antimicrobial pouch constructed as above can efficiently release the antimicrobial substance to atmosphere using vibration or shock when carrying the antimicrobial pouch.

In other words, the antimicrobial pouch of the invention stably releases an appropriate amount of the antimicrobial substance under vibration or shock. Hence, the antimicrobial pouch of the invention is very suitable for carrying on a person's body.

For example, the release hole is provided at an edge portion of the second pouch body.

In an exemplary embodiment of the invention, the second pouch body is manufactured by stacking two sheets of light blocking films and pressure-bonding the periphery of the light blocking films.

Due to such a construction, it is easy to manufacture a flat antimicrobial pouch, which is easy to carry while suspending it around a neck or putting it into a pocket.

Also, since the peripheral pressure-bonding section is strong, the shape is not easily deformed even under vibration or shock while carrying the antimicrobial pouch. Therefore, a risk such as leakage of contents due to the damage of the pouch or the like is small.

In an exemplary embodiment of the invention, the release hole is further provided in the contact portion of the second pouch body.

In the second pouch body, by providing the release hole in the contact portion between the first pouch body and the second pouch body, an air flow passage is formed within the second pouch body through the release hole formed in the region where the space is formed between the first pouch body and the second pouch body, and the release hole formed in the contact portion, thereby stably releasing the antimicrobial substance.

For example, the plurality of release holes are provided, and at least a part of the respective release holes are provided at the edge portion of the second pouch body.

In an exemplary embodiment of the invention, the second pouch body has a flat polygonal shape.

Also, in this case, the release holes can be provided at edge portions of a plurality of rectangular sides.

By providing the release holes at the edge portions of the plurality of rectangular sides, an air flow passage can be secured even in a stationary state, and thus, the antimicrobial substance can be efficiently released.

Also, in an exemplary embodiment of the invention, the second pouch body has a flat circular or oval shape, and the plurality of release holes release holes at an edge portion at intervals.

By providing the plurality of release holes release holes at circular or oval edge portions at intervals, an air flow passage can be secured even in a stationary state, and thus, the antimicrobial substance can be efficiently released.

Also, in an exemplary embodiment of the invention, the release holes are provided at both sides of the second pouch body, that is, the front and rear surfaces of the second pouch body.

By providing the release holes at both sides of the second pouch body, that is, the front and rear surfaces of the second pouch body, an air flow passage can be secured more efficiently even in a stationary state.

Also, in an exemplary embodiment of the invention, the release holes of the front surface and the release holes of the rear surface are provided at edge portions of different sides of the second pouch body.

Accordingly, since air inside the second pouch body is efficiently circulated, the antimicrobial substance can be released more efficiently.

In an exemplary embodiment of the invention, a volume ratio of the first pouch body to the second pouch body is 1:3 to 1:1.2.

By setting the volume ratio of the first pouch body to the second pouch body as above, a space can be appropriately formed between the first pouch body and the second pouch body. Therefore, when vibration or shock is applied, the antimicrobial substance can be released more stably from the first pouch body.

In an exemplary embodiment of the invention, the inorganic solid carrier is a particle having an average particle size of 0.01 to 1 mm. In the first pouch body, a filling rate of the inorganic solid carrier is 30 to 80%.

By providing the inorganic solid carrier having a relatively small particle size and setting the filling rate to the above range, the flowability of the particle can be increased, and the antimicrobial substance can be stably released from the first pouch body over a long term.

In an exemplary embodiment of the invention, the release hole is blocked by a peelable seal.

Due to such a construction, when not in use, the release of the antimicrobial substance from the release hole can be blocked. Therefore, it is suitable for portable use.

In an exemplary embodiment of the invention, the antimicrobial substance is chlorine dioxide, and the inorganic solid carrier is at least one selected from sepiolite, zeolite, silica, alumina, and silica alumina.

By using these inorganic solid carriers, the appropriate adsorption of the antimicrobial substance can be realized.

In an exemplary embodiment of the invention, it is possible to provide a solid antimicrobial agent suitable for portable use, which is capable of continuously releasing a stable amount of chlorine dioxide even under vibration or shock. Also, in an exemplary embodiment, the antimicrobial effect can be stabilized over a long term.

DETAILED DESCRIPTION OF THE PREFERRED EMBODIMENTS

First Embodiment

Hereinafter, an antimicrobial pouch according to a first embodiment of the invention will be described with reference to FIGS. 1 to 4.

Figure 1:
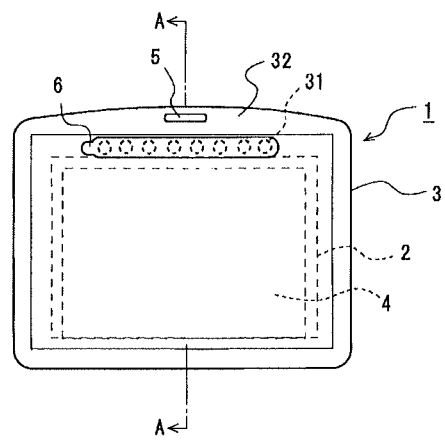
FIG. 1 is a front view illustrating an antimicrobial pouch according to a first embodiment of the invention.

An antimicrobial pouch 1 illustrated in FIG. 1 includes a pouch body 2 (first pouch body) made of a non-woven fabric, and a pouch body (second pouch body) 3 made of an aluminum-evaporated film and receiving the pouch body 2. In the pouch body 2, a solid particulate antimicrobial agent 4 is received at a filling rate of about 60% of the volume of the pouch body 2.

In a state in which the antimicrobial agent 4 is not received, the pouch body 2 has a rectangular sheet shape (45 mm (length)×65 mm (width) (inner space formation region)). The pouch body 2 is manufactured by folding a sheet of a non-woven fabric in two and attaching the peripheral region of the folded non-woven fabric.

Fine holes (not illustrated) having a diameter smaller than a diameter of sepiolite fine particles are formed in the whole surface of the pouch body 2. The fine holes do not transmit sepiolite fine particles but transmit chlorine dioxide molecules.

In a state in which the pouch body 2 receiving the antimicrobial agent 4 is not received, the pouch body 3 has a rectangular sheet shape (55 mm (length)×85 mm (width) (inner space formation region)). The pouch body 3 is manufactured by stacking two sheets of aluminum-evaporated films and pressure-bonding the peripheral region of the stacked films.

Also, a pressure bonding section 32 of the long side of the pouch body 3 is wide in the center, and an elongate hole 5 for suspending a strap (not illustrated) is formed in the center. The pouch body 3 can be made of any material as long as the material does not substantially transmit the antimicrobial substance. Also, a light blocking material can be used in terms of maintaining the stability of the antimicrobial substance.

The pouch body 3 has about 1.6 times the volume of the pouch body 2. Also, the volume when using such a flat pouch body of the embodiment may be approximated to a front area of the pouch body (region corresponding to the inner space formation region).

Herein, the volume ratio of the pouch body 2 to the pouch body 3 may be about 1:3 to 1:1.2, and more preferably about 1:2 to 1:1.2. By setting the volume ratio to the above range, an appropriate space may be formed between the pouch body 2 and the pouch body 3, and a slow release of the antimicrobial agent to the atmosphere may be secured, which will be described later in detail. In particular, since the flat pouch body 3 is used, an appropriate space may be formed at a predetermined position of the pouch body 2 and the pouch body 3. An operation and effect of the space will be described later in detail.

Since the flat pouch body 3 is used and the entire antimicrobial pouch 1 is formed in a flat shape, the antimicrobial pouch 1 can be worn around a neck or can be put in a pocket. Therefore, the antimicrobial pouch 1 is easy to carry. A maximum thickness of the antimicrobial pouch 1 (thickness at the thickest region, thickness at a portion near the center in the embodiment) may be preferably about 3 mm to 10 mm, and more preferably about 3 mm to 8 mm.

Also, since the pouch body 3 has a flat shape and additionally the pressure-bonding section of the peripheral region is strong, the pouch body 3 is not greatly deformed, even though shock is applied while carrying the pouch 1. Therefore, a risk that the deformation of the pouch body 3 due to the shock causes the antimicrobial agent 4 to leak out or causes a large amount of chlorine dioxide molecules to be released at a time is small.

In the pouch body 3, eight release holes 31 having a diameter of about 4 mm are provided in an edge portion of the long side.

The release holes 31 are blocked by a peelable seal 6. When using the antimicrobial pouch, the seal 6 is peeled off to open the release holes 31 (see FIG. 2).

The antimicrobial agent 4 is prepared by physically adsorbing and supporting chlorine dioxide onto porous fine particles (average particle size of 0.1 mm) made of sepiolite or the like. A method of adsorbing chloride dioxide onto an inorganic solid carrier of sepiolite or the like is known (see JP-A No. 6-233985). For example, an inorganic acid is added to a chlorous acid aqueous solution, and a generated mixture is cleaned by a sodium chlorite aqueous solution. Chlorine in the mixture is converted into chloride dioxide. The generated chloride dioxide is adsorbed onto the inorganic solid carrier.

In the antimicrobial agent 4, the chloride dioxide is dissociated from sepiolite by a physical force, such as a vibration of the surrounding atmosphere or the like, or a collision between fine particles.

Herein, the average particle size (median size) of the inorganic solid carrier made of sepiolite or the like is preferably in a range of 0.01 to 1 mm. Also, in the embodiment, the average particle size may be measured by an apparatus using a principle of a laser diffraction and scattering method.

By setting the average particle size in a predetermined range, the flowability of the antimicrobial agent 4 may be controlled, and the release of the antimicrobial substance from the first pouch body may be stably continued. Furthermore, from the viewpoint of further improving effects, the filling rate of the inorganic solid carrier in the first pouch body may be about 30 to 80%, and more preferably about 40 to 70%. The filling rate in the embodiment may be calculated by dividing the apparent volume when the antimicrobial agent is filled under non-compression by the volume of the first pouch body.

As the flowability is higher, also, as the filling rate is lower, the release of the antimicrobial substance is easily progressed.

Next, a release mechanism of the chlorine dioxide according to the embodiment will be described with reference to FIG. 4.

Figure 4:
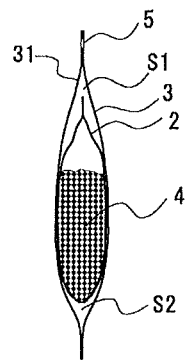
FIG. 4 is a cross-sectional view taken along line A-A of FIG. 1.

FIG. 4 is a cross-sectional view taken along line A-A of FIG. 1.

Chlorine dioxide supported in sepiolite fine particles constituting the antimicrobial agent 4 is dissociated from the surface of the fine particle due to an air flow generated by a vibration of the antimicrobial pouch 1, or a collision between the fine particles constituting the antimicrobial agent 4, and is released to the outside of the pouch body 2 from the fine holes formed on the entire surface of the pouch body 2 made of a non-woven fabric. In a normal state, the pouch body 2 receiving the antimicrobial agent 4 is thickest in a portion near the center and contacts the inside of the pouch body 3. On the other hand, the pouch body 2 receiving the antimicrobial agent 4 is thinner as it goes to the edge portion, and a space S1 and a space S2 are formed between the pouch body 2 and the pouch body 3 having a volume larger than the pouch body 2. Chlorine dioxide released from the fine holes of the pouch body 2 is temporarily retained in the space S1 and is slowly released from the release holes 31 of the pouch body 3. Also, chlorine dioxide temporarily retained in the space S2 is slowly diffused to the space S1 within the pouch body 3 and is slowly released from the release holes 31.

Herein, the case in which possible shock or vibration generated when carrying the pouch is applied to the antimicrobial pouch 1 will be described. If shock or vibration is applied, air around the antimicrobial agent 4 may be vibrated or collide with the fine particles of the antimicrobial agent 4. Hence, as compared to a stationary state, a lot of chlorine dioxide is dissociated from the fine particles. The dissociated chlorine dioxide is released from the fine holes of the pouch body 2 to the space S1 and the space S2 and is retained in the spaces. Chlorine dioxide retained in the space S1 communicating with the release hole 3 is slowly released from the release hole 31.

If the release hole is provided at not the edge portion of the pouch body 3 (portion forming the space) but, for example, a portion near the center (contact portion), an effect that retains chlorine dioxide in the space is not sufficiently obtained. Therefore, when strong shock is applied, chlorine dioxide may be released at a time. This is because the strongest shock is easily applied to the central portion in which the pouch body 3 is thickest.

Also, in the case of the embodiment, even when a pressure is applied to the edge portion of the pouch body 3, only chlorine dioxide retained in the space S1 is released at a time. Therefore, a risk that releases more than a predetermined amount of chlorine dioxide at a time can be avoided.

However, in the embodiment, pores may be provided in a portion near the center (contact portion). In this case, the size or number of the pores may be adjusted such that chlorine dioxide is not released at a time when shock is applied.

By providing holes in a portion near the center (contact portion) in addition to the edge portion (portion forming a space), an air flow passage can be formed between the edge portion and the portion near the center, and thus, chlorine dioxide can be stably released.

The size of the space may be varied by adjusting the volume ratio of the first pouch body and the second pouch body. As the space is larger, an amount of an antimicrobial agent capable of being released at a time when a pressure is applied to the edge portion is increased. In other words, the volume ratio of the respective pouch bodies may be determined considering a permissible amount or toxicity of the antimicrobial agent used.

Also, in the embodiment, the case of using chlorine dioxide as the antimicrobial agent has been described, but other antimicrobial metals may also be used.

Figure 2:
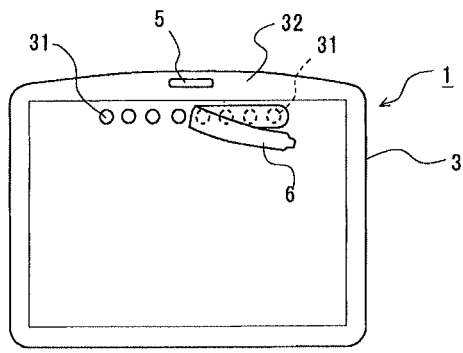
FIG. 2 is a front view illustrating a second pouch body according to the first embodiment of the invention.
Figure 3:
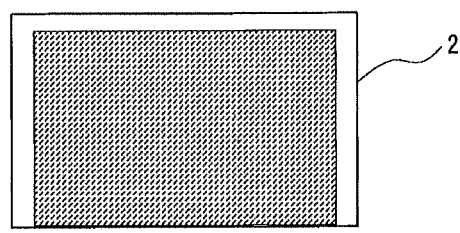
FIG. 3 is a front view illustrating a first pouch body according to the first embodiment of the invention.

The antimicrobial pouch 1 opens the release holes 31 by peeling off the seal 6 at the point of use (see FIG. 2). The antimicrobial pouch 1 can be suspended with a strap in the elongate hole 5, so that a user can wear the antimicrobial pouch 1 around a user's neck, and can be placed at any space, such as a room, an inside of a car, a refrigerator, or the like.

Second Embodiment

Figure 5:
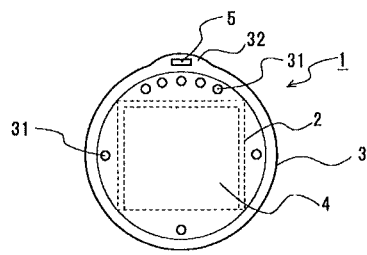
FIG. 5 is a front view illustrating an antimicrobial pouch according to a second embodiment of the invention.

Next, a second embodiment of the invention will be described with reference to FIG. 5.

Also, the same elements as those of the first embodiment described above are denoted by the same reference numerals as those of FIG. 1, and a description thereof will be simplified.

The antimicrobial pouch 1 of the second embodiment includes a pouch body 2 made of a non-woven fabric, and a pouch body 3 made of an aluminum-evaporated film and receiving the pouch body 2. In the pouch body 2, an antimicrobial agent 4 is received at a filling rate of about 60% of the volume of the pouch body 3.

In a state in which the antimicrobial agent 4 is not received, the pouch body 2 has a rectangular sheet shape (33 mm (length)×36 mm (width) (inner space formation region)). Fine holes (not illustrated) having a diameter smaller than a diameter of sepiolite fine particles are formed in the entire surface of the pouch body 2.

In a state in which the pouch body 2 receiving the antimicrobial agent 4 is not received, the pouch body 3 has a circular sheet shape (diameter of 53 mm (inner space formation region)). The pouch body 3 is manufactured by stacking two sheets of aluminum-evaporated films and pressure-bonding the periphery of the stacked films. A portion of the pressure-bonding section 32 of the pouch body 3 is formed widely, and an elongate hole 5 for suspending a strap (not illustrated) is formed in the center.

The pouch body 3 has about 1.9 times the volume of the pouch body 2.

In the pouch body 3, a plurality of release holes 31 having a diameter of about 4 mm are provided at an edge portion, spaced apart from one another in an arc shape. Also, although not illustrated, the release holes 31 may be blocked by a peelable seal.

Also, the pouch body 3 may have an oval shape.

As in the embodiment, by forming the first pouch in a polygonal shape such as a rectangular shape and forming the second pouch in a circular shape, an appropriate space may be formed between the first pouch and the second pouch, which is effectively applied to the effective stable release of the antimicrobial agent. Furthermore, a movement of the first pouch body within the second pouch body is suppressed, contributing to a further stable release of the antimicrobial agent.

Also, according to the embodiment, since a plurality of release holes 31 are provided at intervals in a circumferential direction of the second pouch body, an air flow passage inside the pouch body 3 may be secured even in a stationary state, leading to an efficient release of the antimicrobial substance.

Third Embodiment

Figure 6:
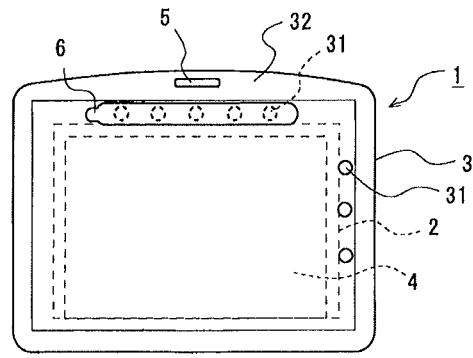
FIG. 6 is a front view illustrating an antimicrobial pouch according to a third embodiment of the invention.

Next, a third embodiment of the invention will be described with reference to FIG. 6.

Also, the same elements as those of the first embodiment described above are denoted by the same reference numerals as those of FIG. 1, and a description thereof will be simplified.

An antimicrobial pouch 1 of the third embodiment includes a pouch body 2 made of a non-woven fabric, and a pouch body 3 made of an aluminum-evaporated film and receiving the pouch body 2. In the pouch body 2, an antimicrobial agent 4 is received at a filling rate of about 60% of the volume of the pouch body 3.

In a state in which the antimicrobial agent 4 is not received, the pouch body 2 has a rectangular sheet shape (65 mm (length)×45 mm (width) (inner space formation region)).

Fine holes (not illustrated) having a diameter smaller than a diameter of sepiolite fine particles are formed in the entire surface of the pouch body 2.

In a state in which the pouch body 2 including the antimicrobial agent 4 is not received, the pouch body 3 has a rectangular sheet shape (85 mm×55 mm (inner space formation region)). The pouch body 3 is manufactured by stacking two sheets of aluminum-evaporated films and pressure-bonding the peripheral region of the stacked films. A long side of one of the pressure-bonding sections 32 of the pouch body 3 is wide in the center, and an elongate hole 5 for suspending a strap (not illustrated) is formed in the center.

The pouch body 3 has about 1.6 times the volume of the pouch body 2.

In the pouch body 3, a plurality of release holes 31 having a diameter of about 4 mm are provided at an edge portion of the long side and an edge portion of the short side. As such, by providing the release holes 31 in the plurality of rectangular sides, an air flow passage inside the pouch body 3 can be secured even in a stationary state, leading to an efficient release of the antimicrobial substance.

Fourth Embodiment

Figure 7:
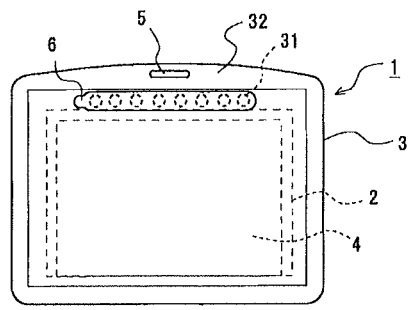
FIG. 7 is a front view illustrating an antimicrobial pouch according to a fourth embodiment of the invention.
Figure 8:
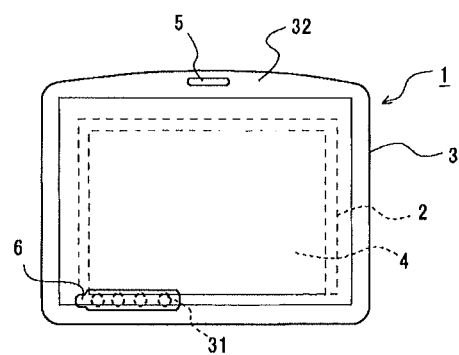
FIG. 8 is a rear view illustrating the antimicrobial pouch according to the fourth embodiment of the invention.

Next, a fourth embodiment of the invention will be described with reference to FIGS. 7 and 8.

Also, the same elements as those of the first embodiment described above are denoted by the same reference numerals as those of FIG. 1, and a description thereof will be simplified.

An antimicrobial pouch 1 of the fourth embodiment includes a pouch body 2 made of a non-woven fabric, and a pouch body 3 made of an aluminum-evaporated film and receiving the pouch body 2. In the pouch body 2, an antimicrobial agent 4 is received at a filling rate of about 60% of the volume of the pouch body 3.

In a state in which the antimicrobial agent 4 is not received, the pouch body 2 has a rectangular sheet shape (33 mm (length)×36 mm (width) (inner space formation region)).

Fine holes (not illustrated) having a diameter smaller than a diameter of sepiolite fine particles are formed in the whole surface of the pouch body 2.

In a state in which the pouch body 2 including the antimicrobial agent 4 is not received, the pouch body 3 has a rectangular sheet shape (85 mm×55 mm (inner space formation region)). The pouch body 3 is manufactured by stacking two sheets of aluminum-evaporated films and pressure-bonding the peripheral region of the stacked films. A long side of one of the pressure-bonding sections 32 of the pouch body 3 is wide in the center, and an elongate hole 5 for tying a strap (not illustrated) is formed in the center.

The pouch body 3 has about 1.6 times the volume of the pouch body 2.

In the pouch body 3, a plurality of release holes 31 having a diameter of about 4 mm are provided at an edge portion of the long side on an upper front surface. Also, a plurality of release holes 31 having a diameter of about 4 mm are provided at an edge portion of the long side on a lower rear surface.

As such, by providing the release holes in the different sides of the front surface and the rear surface, an air flow passage inside the pouch body 3 can be secured even in a stationary state, leading to an efficient release of the antimicrobial substance.

Embodiments

First Experimental Example

A fruit (tangerine) decay test was performed using the antimicrobial pouch manufactured as above according to the first embodiment.

The tangerine was divided in half and put into three hermetically-sealed containers. The antimicrobial pouch of the first embodiment was put into the two containers (sample 1, sample 2), and no antimicrobial pouch was put into the other one (control). The hermetically-sealed container of the sample 1 was shaken several times a day, and the hermetically-sealed containers of the sample 2 and the control was in a stationary state. Then, the state of the tangerine was observed with time.

As a result, it was observed that the tangerine put into the hermetically-sealed container of the sample 1, which contained the antimicrobial pouch of the first embodiment, was slightly decayed on its peel even after a lapse of 30 days. Also, it was observed that the tangerine put into the hermetically-sealed container of the sample 2 was slightly decayed on its peel after a lapse of 18 days and mildew was partially formed after a lapse of 30 days. Meanwhile, the tangerine of the hermetically-sealed container, which contained no antimicrobial pouch, was partially covered with mildew and blue mold on the twelfth day, and was fully covered with blue mold on the eighteenth day.

From the above results, it was confirmed that the antimicrobial pouch of the invention exerted a long-term stable antimicrobial effect. In particular, it was observed that the effect was exerted over a longer term when the antimicrobial pouch was periodically shaken.

Experimental Example 2

A fruit (tangerine) decay test was performed using the antimicrobial pouch manufactured as above according to the third embodiment.

The tangerine was divided in half and put into a hermetically-sealed container which contained the antimicrobial pouch of the third embodiment (sample 3). The hermetically-sealed container of the sample 3 was in a stationary state, and the state of the tangerine was observed with time.

As a result, it was observed that the tangerine put into the hermetically-sealed container of the sample 3, which contained the antimicrobial pouch of the third embodiment, was slightly decayed on its peel even after a lapse of 30 days.

From the above results, it was confirmed that due to the release holes provided in the plurality of rectangular sides, the antimicrobial substance was stably released even in a stationary state, and a long-term stable antimicrobial effect was exerted.

Since the antimicrobial pouch of the invention can exert a continuous antimicrobial effect and can also be safely carried, all persons can wear the antimicrobial pouch in a meeting place or the like where a lot of persons gather. Therefore, virus infection or bacterial infection can be prevented.

What is claimed is:

1. An antimicrobial pouch for portable use comprising:
   an antimicrobial agent supporting an antimicrobial substance in a porous inorganic solid carrier;
   a first pouch body receiving the antimicrobial agent; and
   a second pouch body receiving the first pouch body,
   wherein the first pouch body has a flat shape, and comprises fine holes on an entire surface, the fine holes having a diameter smaller than a particle size of the inorganic solid carrier,
   the second pouch body comprises two sheets of light blocking films bonded to each other at a bonding portion formed along a whole periphery of the light blocking films, and has a flat shape, and has regions where both sides of the first pouch body contact an inside of the second pouch body, and a region where a space is formed between the first pouch body and the second pouch body,
   the second pouch body further comprises a hanging hole provided on the bonding portion, and a release hole through which the antimicrobial substance is released to atmosphere when the antimicrobial pouch is carried, and
   the release hole is provided at an edge portion of the second pouch body adjacent to the hanging hole at the region of the second pouch body where the space is formed.

2. The antimicrobial pouch according to claim 1, wherein the second pouch body is manufactured by pressure-bonding the periphery of the light blocking films.

3. The antimicrobial pouch according to claim 1, wherein the second pouch body has a flat polygonal shape.

4. The antimicrobial pouch according to claim 1, wherein a volume ratio of the first pouch body to the second pouch body is 1:3 to 1:1.2.

5. The antimicrobial pouch according to claim 1, wherein the inorganic solid carrier is a particle having an average particle size of 0.01 to 1 mm, and a filling rate of the inorganic solid carrier in the first pouch body is 30 to 80%.

6. The antimicrobial pouch according to claim 1, wherein the release hole is blocked by a peelable seal.

7. The antimicrobial pouch according to claim 1, wherein the antimicrobial substance is chlorine dioxide, and the inorganic solid carrier is at least one selected from sepiolite, zeolite, silica, alumina, and silica alumina.

8. An antimicrobial pouch for portable use comprising:
   an antimicrobial agent supporting an antimicrobial substance in a porous inorganic solid carrier;
   a first pouch body receiving the antimicrobial agent; and
   a second pouch body receiving the first pouch body,
   wherein the first pouch body has a flat shape, and comprises fine holes on an entire surface, the fine holes having a diameter smaller than a particle size of the inorganic solid carrier,
   the second pouch body comprises two sheets of light blocking films bonded to each other at a bonding portion formed along a whole periphery of the light blocking films, and has a flat shape, and has regions where both sides of the first pouch body contact an inside of the second pouch body,
   the second pouch body further comprises a hanging hole provided on the bonding portion, and a row of release holes through which the antimicrobial substance is released to atmosphere when the antimicrobial pouch is carried, and
   the row of release holes are provided at an edge portion of the second pouch body adjacent to the hanging hole of the second pouch body.

9. The antimicrobial pouch according to claim 8, wherein the second pouch body is manufactured by pressure-bonding a periphery of the light blocking films.

10. The antimicrobial pouch according to claim 8, wherein the second pouch body has a flat polygonal shape.

11. The antimicrobial pouch according to claim 8, wherein a volume ratio of the first pouch body to the second pouch body is 1:3 to 1:1.2.

12. The antimicrobial pouch according to claim 8, wherein the inorganic solid carrier is a particle having an average particle size of 0.01 to 1 mm, and a filling rate of the inorganic solid carrier in the first pouch body is 30 to 80%.

13. The antimicrobial pouch according to claim 8, wherein the release holes are blocked by a peelable seal.

14. The antimicrobial pouch according to claim 8, wherein the antimicrobial substance is chlorine dioxide, and the inorganic solid carrier is at least one selected from sepiolite, zeolite, silica, alumina, and silica alumina.

15. The antimicrobial pouch according to claim 8, wherein the two sheets of light blocking films comprise first and second light blocking films, the row of release holes are provided on an upper part of the first film along the bonding portion, and a second row of release holes are provided on a lower part of the second film along the bonding portion.

* * * * *